United States Patent [19]

Singh et al.

[11] Patent Number: 5,256,657
[45] Date of Patent: Oct. 26, 1993

[54] SUCCINAMIDE DERIVATIVE MATRIX-METALLOPROTEASE INHIBITORS

[75] Inventors: Jasbir Singh, Albany; Barry A. Morgan, Colonie; James A. Gainor, Bethlehem; Thomas D. Gordon, Schodack; Robert C. Wahl, Rochester, all of N.Y.

[73] Assignee: Sterling Winthrop, Inc., New York, N.Y.

[21] Appl. No.: 747,887

[22] Filed: Aug. 19, 1991

[51] Int. Cl.$^5$ .............. A61K 31/215; A61K 31/38; A61K 31/405; A61K 31/415; A61K 31/16; A61K 31/44; C07D 279/16; C07D 413/12; C07D 409/12; C07D 401/12; C07C 321/04; C07C 235/02

[52] U.S. Cl. .............. 514/228.2; 514/212; 514/227.5; 514/227.8; 514/235.2; 514/235.8; 514/235.5; 514/237.2; 514/231.5; 514/237.8; 514/252; 514/253; 514/255; 514/318; 514/315; 514/343; 514/357; 514/397; 514/400; 514/414; 514/419; 514/422; 514/424; 514/438; 514/319; 514/326; 514/428; 514/562; 514/616; 540/597; 540/602; 540/603; 540/596; 540/610; 544/58.1; 544/58.5; 544/58.6; 544/58.7; 544/59; 544/60; 544/62; 544/131; 544/139; 544/143; 544/145; 544/159; 544/160; 544/360; 544/370; 544/373; 544/379; 544/400; 546/192; 546/193; 546/194; 546/201; 546/208; 546/212; 546/213; 546/247; 546/281; 546/335; 548/336; 548/342; 548/467; 548/495; 548/527; 548/550; 548/568; 549/76; 549/77; 562/426; 562/430; 564/153; 564/154

[58] Field of Search .............. 564/153, 154; 562/426, 562/430; 548/568, 336, 342, 467, 495, 527, 550; 514/318, 319, 326, 616, 562, 428, 212, 227.5, 227.8, 228.2, 235.2, 235.8, 235.5, 237.2, 231.5, 237.8, 252, 253, 255, 315, 343, 357, 397, 400, 414, 419, 422, 424, 438; 546/192, 193, 194, 201, 208, 212, 213, 247, 281, 335; 540/597, 602, 603, 596, 610; 544/58.1, 58.5, 58.6, 58.7, 59, 60, 62, 131, 139, 143, 145, 160, 159, 360, 370, 373, 379, 400; 549/76, 77

[56] References Cited

FOREIGN PATENT DOCUMENTS

WO90/05716 5/1990 PCT Int'l Appl. .
WO90/02716 3/1991 PCT Int'l Appl. .

*Primary Examiner*—Johann Richter
*Attorney, Agent, or Firm*—Liza D. Hohenschutz

[57] ABSTRACT

Compounds having the structural formula $$X-\overset{O}{\underset{}{C}}-CH(CH_2R^1)-CH(CH_2R^2)-\overset{O}{\underset{}{C}}-NH-(CH_2)_m-SO_n-(CH_2)_p-NR^3R^4 \quad \text{Formula I}$$

wherein X is HONH or HO and especially wherein the carbon atom bearing $CH_2R^1$ has the R-configuration, the carbon atom bearing $CH_2R^2$ has the S-configuration, $R^1$ is isopropyl, $R^2$ is 3-indolyl, m is 2, n is 0, p is 2 and $R^3$ and $R^4$ taken alone are each methyl or $R^3$ and $R^4$ taken together with N are morpholino and pharmaceutically acceptable acid addition salts or solvates or acid addition salts-solvates thereof, which are matrix-metalloprotease inhibitors useful in treatment of disease in which matrix-metalloprotease promoted connective tissue remodelling is a causative factor, for example, rheumatoid arthritis and cancer, and a method of preparation and method of use thereof and methods of preparation of intermediates therefor are disclosed.

11 Claims, No Drawings

SUCCINAMIDE DERIVATIVE MATRIX-METALLOPROTEASE INHIBITORS

BACKGROUND OF THE INVENTION

1. Field of the Invention

The invention relates to succinamide derivative matrix-metalloprotease inhibitors useful in treatment of disease in which matrix-metalloprotease promoted connective tissue remodelling is a causative factor, for example, rheumatoid arthritis and cancer, and to method of preparation and method of use thereof and methods of preparation of intermediates therefor.

2. Information Disclosure Statement

Davidson et al. (British Bio-technology Limited) PCT Application WO 90/05716 published May 31, 1990 describes collagenase inhibitors having the structural formula

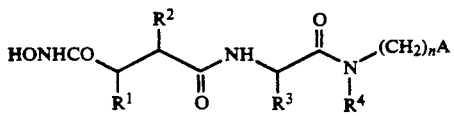

(I)

wherein $R_1$ [sic] represents a hydrogen atom or a $C_1$–$C_6$ alkyl, $C_1$–$C_6$ alkenyl, phenyl, phenyl($C_1$–$C_6$)alkyl, $C_1$–$C_6$ alkylthiomethyl, phenylthiomethyl, substituted phenylthiomethyl, phenyl($C_1$–$C_6$)alkylthiomethyl or heterocyclylthiomethyl group; or $R^1$ represents —$SR^x$ wherein $R^x$ represents a group (a);

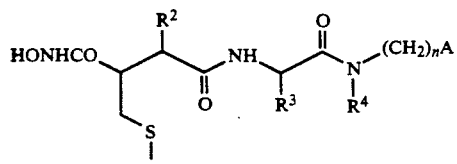

(a)

$R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl($C_1$–$C_6$)alkyl; $R^3$ represents an amino acid residue with R or S stereochemistry of a $C_1$–$C_6$ alkyl, benzyl, ($C_1$–$C_6$)alkoxybenzyl or benzyloxy($C_1$–$C_6$)alkyl group; $R^4$ represents a hydrogen atom or a methyl group; n is an integer from 1 to 6; and A represents the group —$NH_2$, a substituted acyclic amine or a heterocyclic base; or a salt and/or N-oxide and/or (where the compound is a thio-compound) a sulphoxide or sulphone thereof . . .

and the corresponding compounds having the structural formula

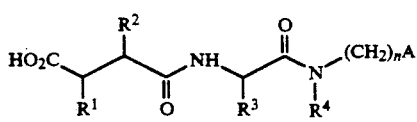

(IV)

useful as intermediates for preparing the compounds of formula (I).

Campion et al. (British Bio-technology Limited) PCT Application WO 91/02716 published Mar. 7, 1991 describes collagenase inhibitors having the structural formula

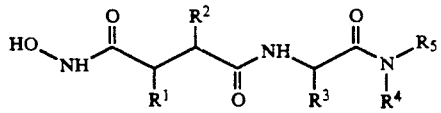

(I)

wherein $R^1$ represents a hydrogen atom or a $C_1$–$C_6$ alkyl, $C_1$–$C_6$ alkenyl, phenyl, phenyl($C_1$–$C_6$)alkyl, $C_1$–$C_6$ alkylthiomethyl, phenylthiomethyl, substituted phenylthiomethyl, phenyl($C_1$–$C_6$)alkylthiomethyl or heterocyclylthiomethyl group; or $R^1$ represents —S—$R^x$ wherein $R^x$ represents a group a;

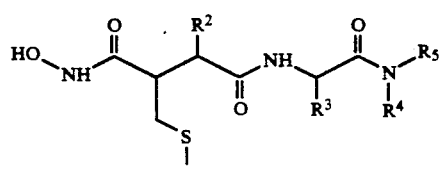

(a)

$R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl, or cycloalkenyl($C_1$–$C_6$)alkyl; $R^3$ represents an amino acid side chain or a $C_1$–$C_6$ alkyl, benzyl, ($C_1$–$C_6$)alkoxybenzyl, benzyloxy($C_1$–$C_6$)alkyl or benzyloxybenzyl group; $R^4$ represents a hydrogen atom or a methyl group; $R^5$ represents a group $(CH_2)_nA$; or $R^4$ and $R^5$ together represent a group $\beta$;

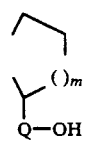

($\beta$)

Q represents $CH_2$ or CO; m is an integer from 1 to 3; n is an integer from 1 to 6; and A represents a hydroxy, ($C_1$–$C_6$)alkoxy, ($C_2$–$C_7$)acyloxy, ($C_1$–$C_6$)alkylthio, phenylthio, ($C_2$–$C_7$)acylamino or N-pyrrolidone group or a salt and/or N-oxide and/or (where the compound is a thio-compound) a sulphoxide or sulphone thereof . . .

and the corresponding compounds having the structural formula

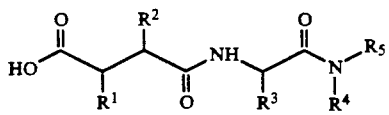

(IV)

useful as intermediates for preparing the compounds of formula (I).

SUMMARY OF THE INVENTION

In a composition of matter aspect the invention is a compound having the structural formula

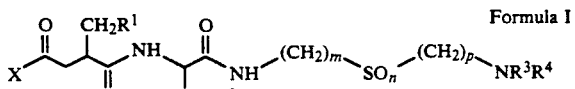

Formula I wherein
X is HONH or HO;

$R^1$ is alkyl having from one to six carbon atoms;

$R^2$ taken together with $CH_2$ is the side chain of a natural amino acid or taken alone is alkyl having from one to six carbon atoms, phenyl or phenyl-lower-alkyl wherein phenyl can be substituted by hydroxy or lower-alkoxy, or monoheterocyclyl, monoheterocyclyl-lower-alkyl, biheterocyclyl or biheterocyclyl-lower-alkyl wherein each heterocyclyl has five or six ring atoms and the heteroatom is a nitrogen, oxygen or sulfur atom and can additionally be one or two nitrogen atoms;

$R^3$ taken alone is alkyl having from one to six carbon atoms;

$R^4$ taken alone is H or alkyl having from one to three carbon atoms; or, when $R^3$ and $R^4$ are both alkyl, the tertiary amine N-oxide; or $R^3$ and $R^4$ taken together with N are pyrrolidino, piperidino, azepino, morpholino or thiomorpholino or the N-oxide thereof or piperazino or N-methyl-piperazino;

m is an integer from 2 to 6;

n is 0, 1 or 2;

p is an integer from 2 to 6; or a pharmaceutically acceptable acid addition salt or solvate or acid addition salt-solvate thereof.

The compounds of Formula I are matrix-metalloprotease inhibitors useful in treatment of disease in which matrix-metalloprotease promoted connective tissue remodelling is a causative factor, for example, rheumatoid arthritis and cancer.

In a first process aspect the invention is the process for preparing a compound of Formula I which comprises condensing the corresponding compound having the structural formula

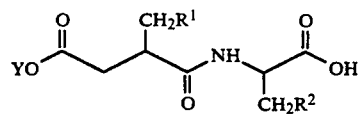

Formula II wherein Y is a carboxy protecting group with the corresponding compound having the structural formula

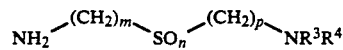

Formula III by a peptide coupling method, then removing Y to form the corresponding compound of Formula I wherein X is HO, then condensing the corresponding compound of Formula I wherein X is HO with O-protected or unprotected hydroxylamine by a peptide coupling method and removing the hydroxylamine O-protecting group if present to form the corresponding compound of Formula I wherein X is HONH.

In a second process aspect the invention is the process for preparing a compound of Formula II which comprises condensing the corresponding compound having the structural formula

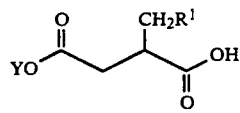

Formula IV with the corresponding compound having the structural formula

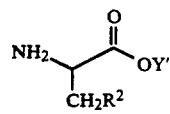

Formula V wherein Y' is a carboxy protecting group by a peptide coupling method, then removing Y'.

In a third process aspect the invention is the process for preparing a compound of Formula IV which comprises condensing the lithium salt of the corresponding compound having the structural formula

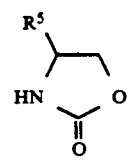

Formula VI wherein $R^5$ is isopropyl or benzyl with the corresponding compound having the structural formula

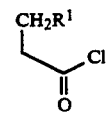

Formula VII to form the corresponding compound having the structural formula

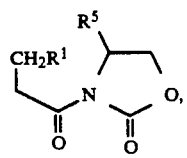

Formula VIII then condensing the lithium salt of the compound of Formula VIII with the corresponding compound having the structural formula

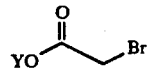

Formula IX to form the corresponding compound having the structural formula

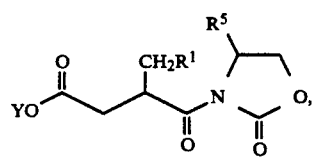

Formula X then hydrolyzing the amide bond of the compound of Formula X with aqueous lithium hydroxide and hydrogen peroxide and reducing the resulting peracid to form the compound of Formula IV.

In a fourth process aspect the invention is the method of treating a mammal for a disease in which matrix-metalloprotease promoted connective tissue remodelling is a causative factor which comprises administering to the mammal a matrix-metalloprotease inhibiting amount of a compound of Formula I.

DETAILED DESCRIPTION OF THE INVENTION INCLUSIVE OF THE PREFERRED EMBODIMENTS

Definitions

In the compounds of Formulas I–X "corresponding" means that a defined variable in one formula has the same definition in another formula.

Alkyl of one to three carbon atoms and alkyl of one to six carbon atoms can be branched or unbranched. Alkyl of one to six carbon atoms is preferably primary or secondary. $R^1$ is preferably isopropyl.

In $R^2$ lower-alkyl or lower-alkoxy has one to three carbon atoms. When $R^2$ is heterocyclyl, it is, for example, pyridyl, thienyl, imidazolyl or indolyl, preferably indolyl, most preferably 3-indolyl, and the amino acid moiety of which it is part is accordingly tryptophyl.

The carbon atom bearing $CH_2R^1$ preferably has the R-configuration. The carbon atom bearing $CH_2R^2$ preferably has the S-configuration.

Preparation of the Compounds

The acid addition salts of the compounds of Formula I are prepared by conventional methods from any of the pharmaceutically acceptable organic and inorganic acids. Of the inorganic acids hydrochloric acid and phosphoric acid are preferred. Of the organic acids acetic acid is preferred.

The compounds of Formula I and the acid addition salts thereof are hydrophilic and may form solvates with water or hydrophilic organic solvents or mixtures thereof. If the resulting products are crystalline, they are purified by recrystallization. If non-crystalline, they are purified by high pressure liquid chromatography or column chromatography and/or isolated by lyophilization.

The compounds of Formulas II–X and the reagents of the process aspects of the invention are known classes of compounds and are commercially available or can be made by methods specifically or generally described in the chemical literature or by the methods described herein.

The peptide coupling method of the first and second process aspects of the invention is carried out using a carboxy-activated derivative of the compound of Formula II or Formula IV or Formula I wherein X is HO, which can be formed with or without being isolated and which can be selected from the acyl halides and pseudohalides, especially the acyl azides; the anhydrides, especially the mixed anhydrides and most especially the mixed anhydride with diphenylphosphinyl chloride or isobutyl chloroformate; derivatives formed by addition reactions, especially using dicyclohexylcarbodiimide; displaceable acyl derivatives of heterocyclic nitrogen, especially N,N′-carbonyldiimidazole; ring-openable activated heterocyclic systems; acylphosphonium derivatives; and activated esters, especially 1-hydroxybenzotriazole, N-hydroxysuccinimide and pentafluorophenyl esters.

The carboxy protecting group Y or Y′ can be a carboxylate salt, which can be reconverted to carboxylic acid by acidification, the t-butyl ester, which can be removed by acidic cleavage, for example, with hydrogen chloride or trifluoroacetic acid in a suitable solvent, the benzyl ester, which can be removed by catalytic hydrogenation using palladium as catalyst or the methyl ester, which can be removed by alkaline hydrolysis. When Y′ is selectively removed in the presence of Y, Y′ must be chosen so that Y is not also removed by the same deprotection method.

In the first process aspect of the invention hydroxylamine is preferably O-protected, preferably by trialkylsilyl, most preferably trimethylsilyl, which is removed by hydrolysis during workup of the product.

The compound of Formula III is prepared by condensing the corresponding compound having the structural formula $(CH_3)_3COCONH(CH_2)_mOSO_2CH_3$ with the sodium salt of the corresponding compound having the structural formula $HS(CH_2)_pNR^3R^4$ to form the corresponding compound having the structural formula $(CH_3)_3COCONH(CH_2)_mS(CH_2)_pNR^3R^4$, oxidizing S to SO or $SO_2$ if desired, and removing $(CH_3)_3COCO$.

The third process aspect of the invention can provide either enantiomer of the compound of Formula IV by selection of the appropriate enantiomer of the compound of Formula VI as the starting material. The lithium salt of the compound of Formula VI is prepared using an alkyllithium, preferably n-butyllithium, in an inert solvent at a temperature in the range from $-80°$ C. to $30°$ C. Condensation of the lithium salt of the compound of Formula VI with the compound of Formula VII is carried out in an inert solvent at a temperature in the range from $-80°$ C. to $0°$ C. The lithium salt of the compound of Formula VIII is prepared using a lithium dialkylamide, preferably lithium diisopropylamide, in an inert solvent at a temperature in the range from $-80°$ C. to $30°$ C. Condensation of the lithium salt of the compound of Formula VIII with the compound of Formula IX is carried out in an inert solvent at a temperature in the range from $-80°$ C. to $30°$ C. Hydrolysis of the compound of Formula X with aqueous lithium hydroxide and hydrogen peroxide followed by reduction of the resulting peracid to form the compound of Formula IV is carried out at a temperature in the range from $-20°$ C. to $30°$ C. The preferred reducing agent is sodium sulfite.

In the preparations described below structures of products are inferred from known structures of starting materials and expected courses of preparative reactions. Purification or purity and structural confirmation of starting materials and products are carried out or measured by melting temperature range, optical rotation, elemental analysis, infrared spectral analysis, ultraviolet spectral analysis, mass spectral analysis, nuclear magnetic resonance spectral analysis, gas chromatography, column chromatography, high pressure liquid chromatography, medium pressure liquid chromatography, thin layer chromatography and/or amino acid analysis.

EXAMPLE 1

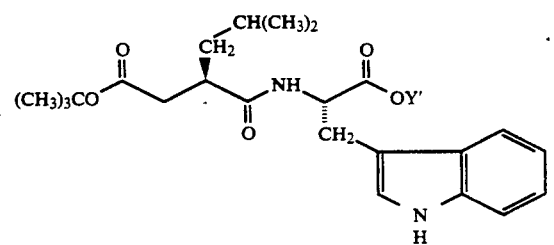

Y′ = $CH_3$     Formula IIa
Y′ = H     Formula IIb

A. A solution of n-butyllithium in hexane (2.5M, 150 mL) was added dropwise during 1¼ h with stirring and cooling to under −60° C. to a solution of the compound of Formula VI wherein $R^5$ is isopropyl having the S-configuration at the carbon atom bearing isopropyl (48.12 g) in tetrahydrofuran (1 L). Stirring was continued for 30 min. 4-Methylpentanoyl chloride (the compound of Formula VII wherein $R^1$ is isopropyl, 48.84 g) was added with continued stirring and cooling. The temperature rose to −45° C. then fell to −65° C. Stirring was continued for 1 h. Aqueous potassium carbonate solution (1M) was added, the tetrahydrofuran was removed under vacuum, water was added to dissolve the precipitate, and the mixture was extracted with ethyl acetate. The ethyl acetate extract was washed with aqueous sodium chloride solution, dried over sodium sulfate and stripped of ethyl acetate. The residue was purified by column chromatography on silica gel with suction using ethyl acetate-hexane (1:5) as eluant affording the compound of Formula VIII wherein $R^1$ and $R^5$ are each isopropyl and the carbon atom bearing $R^5$ has the S-configuration (68.12 g, 83% yield).

B. With stirring and cooling to −70° C. a solution of the entire product of part A of this example in tetrahydrofuran (50 mL) was added to a solution of lithium diisopropylamide in tetrahydrofuran-hexane prepared by adding a solution of n-butyllithium in hexane (2.5M, 127 mL) with stirring and cooling to −10° C. to −20° C. to tetrahydrofuran (700 mL). Stirring and cooling to −70° C. were continued for ½ hr. t-Butyl bromoacetate (the compound of Formula IX wherein Y is t-butyl, 150 g) was added rapidly. The temperature was allowed to rise to and was maintained at 0° C. for 2 h, then lowered to −70° C. again. Saturated aqueous ammonium chloride solution (250 mL) was added, the temperature was allowed to rise to room temperature, and the mixture was stripped of tetrahydrofuran and hexane under vacuum. The residue was extracted with ethyl acetate. The ethyl acetate extract was washed with aqueous sodium chloride solution, dried over sodium sulfate, and stripped of ethyl acetate under vacuum and excess t-butyl bromoacetate under high vacuum. Recrystallization of the resulting crystalline solid from ethyl acetate-hexane gave the compound of Formula X wherein $R^1$ and $R^5$ are each isopropyl, Y is t-butyl and the carbon atom bearing $R^1CH_2$ has the R-configuration in three crops (63.8 g, 10.5 g., 2.9 g; 77.2 g total; 75.4% yield).

C. With stirring and cooling to 0° C. aqueous hydrogen peroxide (30%, 460 mL) was added to a solution of most of the product of part B of this example (77.1 g) in tetrahydrofuran (1525 mL)-water (175 mL). Lithium hydroxide monohydrate (28.41 g) was added, the temperature was allowed to rise to room temperature, and stirring was continued for 4 hr. With continued stirring and dry ice-acetone (−50° C.) cooling to maintain the exothermic reaction temperature at 0°–10° C. sodium sulfite (500 g) was added in portions. The mixture was filtered and the filtrate was extracted with dichloromethane (4×500 mL). The aqueous layer was acidified to pH 7 with solid citric acid and extracted with ethyl acetate, then acidified to pH 5-6 and extracted again with ethyl acetate. Each extract was separately washed with aqueous sodium chloride solution, dried over sodium sulfate, and stripped of ethyl acetate affording the compound of Formula IV wherein $R^1$ is isopropyl, Y is t-butyl and the carbon atom bearing $CH_2R^1$ has the R-configuration (from the first extract 36.7 g of colorless liquid estimated to be pure product (69.5% yield); from the second extract 13.9 g of slightly yellow liquid estimated to be 70% product (19% yield); estimations by proton magnetic resonance spectral analysis).

D. N,N'-Carbonyldiimidazole (14.12 g) was added with stirring at room temperature to a solution of part C (20.01 g) of the pure product of part C of this example in tetrahydrofuran (130 mL). Stirring was continued at room temperature for ¾ h, tryptophan methyl ester hydrochloride salt (22.20 g) then ethyldiisopropylamine (15.2 mL) were added, and stirring was continued at room temperature for 5 days. The mixture was stripped of tetrahydrofuran under vacuum, aqueous citric acid solution (5%) was added, and the residue was extracted with ether. The ether extract was washed with aqueous sodium chloride solution, saturated aqueous sodium bicarbonate solution, again with aqueous sodium chloride solution, dried over magnesium sulfate, and stripped of ether under vacuum. The residue was purified by column chromatography on silica gel with suction using ethyl acetate-hexane (2:3) as eluant followed by crystallization from hexane affording the compound of Formula IIa as white crystals (24.2 g, 64% yield).

E. With stirring at room temperature aqueous sodium hydroxide solution (1N, 40 mL) was added to a solution of part (8.08 g) of the product of part D of this example. More methanol (20 mL) was added to remove cloudiness. Stirring was continued at room temperature for 1 h, the mixture was stripped of methanol, and the residue was neutralized with hydrochloric acid (5%, 40 mL) and extracted with ethyl acetate. The ethyl acetate extract was washed with aqueous sodium chloride solution, dried over sodium sulfate, and stripped of ethyl acetate affording the compound of Formula IIb as a solid in quantitative yield (7.75 g).

EXAMPLE 2

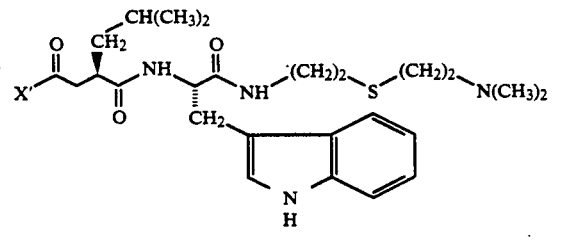

| | |
|---|---|
| X' = t-BuO | Formula Ia |
| X' = X = HO | Formula Ib |
| X' = X = HONH | Formula Ic |

A. N,N-Dimethyl-2,2'-thiobis(ethylamine) dihydrochloride salt (the dihydrochloride salt of the compound of Formula III wherein m is 2, n is 0, p is 2 and $R^3$ and $R^4$ are each methyl) was prepared by reaction of the methanesulfonate ester of 2-(t-butoxycarbonylamino)ethanol with the sodium salt of 2-(dimethylamino)ethanethiol in dimethylformamide at room temperature followed by removal of t-butoxycarbonyl and formation of the dihydrochloride salt with 4N hydrogen chloride in ethyl acetate at room temperature.

N-Hydroxysuccinimide (345 mg) and the compound of Formula IIb (part E of example 1, 1.250 g) were added with stirring at room temperature to a solution of N,N-dimethyl-2,2'-thiobis(ethylamine) dihydrochloride salt (1.01 g) and ethyldiisopropylamine (1.75 mL) in dimethylformamide (15 mL). The reaction mixture was cooled to 0° C., then a solution of dicyclohexylcarbodiimide (620 mg) in dimethylformamide (5 mL) was added. Stirring was continued at 0° C. for 2½ h, then at room temperature overnight. The reaction mixture was concentrated, stripped twice from methanol, then stripped twice from ethyl acetate. The residue was purified first by column chromatography on silica gel by gradient elution with ethyl acetate-pyridine-acetic acid-water (from 700:55:20:25 to 100:55:20:25) then by reverse phase high pressure liquid chromatography on octadecylsilated silica gel by gradient elution with acetonitrile-water containing 0.1% acetic acid (from 5:95 to 95:5). The residue from the fractions containing the product was stripped twice from methanol and dried under high vacuum affording the compound of Formula Ia as a white foam (1.250 g, 76.3% yield).

B. A solution of part (1.0 g) of the product of part A of this example in trifluoroacetic acid-water (70:30, 30 mL) was stirred at room temperature under argon for 3 h and concentrated under vacuum. The residue was stripped twice from methanol then dried over phosphorous pentoxide and potassium hydroxide under high vacuum affording the trifluoroacetate salt of the compound of Formula Ib as a white foam (1.0 g, 92% yield), part (125 mg) of which was lyophilized first from acetic acid and then from t-butyl alcohol affording the trifluoroacetate salt hemihydrate of the compound of Formula Ib as a white lyophil (95 mg).

C. With stirring at −20° C. under argon isobutyl chloroformate (400 μL) was added to a solution of part (885 mg) of the product of part B of this example and N-methylmorpholine (340 μL) in dimethylformamide (5 mL). After 10 min hydroxylamine trimethylsilyl ether (450 μL) was added. Stirring was continued at −20° C. for 1½ h, the temperature was then allowed to rise to room temperature during ½ h, and the reaction mixture was concentrated under vacuum. The residue was striped three times from methanol and purified by column chromatography on silica gel by gradient elution with acetonitrile-acetic acid-water (from 15:1:1 to 4:1:1). The residue from the fractions containing the product was stripped twice from methanol and twice from ether and dried under high vacuum affording the acetate salt of the compound of Formula Ic as an off-white or pale-yellow solid (720 mg, 87% yield).

EXAMPLE 3

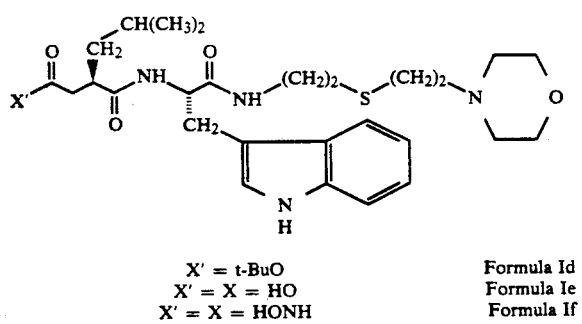

X' = t-BuO  Formula Id
X' = X = HO  Formula Ie
X' = X = HONH  Formula If

A. 2-(2-Morpholinoethylthio)ethylamine dihydrochloride salt (the dihydrochloride salt of the compound of Formula III wherein m is 2, n is 0, p is 2 and $R^3$ and $R^4$ taken together with N are morpholino) was prepared by reaction of N-(t-butoxycarbonyl)cysteamine with N-(2-chloroethyl)morpholine in the presence of 1,8-diazabicyclo[5.4.0]undec-7-ene (DBU) in dimethylformamide at room temperature followed by removal of t-butoxycarbonyl and formation of the dihydrochloride salt with 4N hydrogen chloride in ethyl acetate and dioxane as cosolvent at room temperature.

N-Hydroxysuccinimide (173 mg) and the compound of Formula IIb (part E of example 1,500 mg) were added with stirring under argon at room temperature to a solution of 2-(2-morpholinoethylthio)ethylamine dihydrochloride salt (474 mg) and ethyldiisopropylamine (0.63 mL) in dimethylformamide (13 mL). The reaction mixture was cooled to 0° C., dicyclohexylcarbodiimide (248 mg) was added, and stirring was continued for 7 h. The reaction mixture was filtered and the precipitate was washed with dichloromethane. The filtrate was concentrated under vacuum. The residue was purified by column chromatography on silica gel using ethyl acetate-pyridine-acid-water as eluant (1200:55:20:25, 455 mL; 1000:55:20:25, 495 mL: 800:55:20:25, 495 mL). The fractions containing the product were stripped twice from ether and lyophilized from t-butyl alcohol affording the compound of Formula Id as a white lyophyl (554 mg, 78% yield).

B. A solution of most (500 mg) of the product of part A of this example in trifluoroacetic acid-water (70:30, 25 mL) was stirred at room temperature under argon for 3 h and concentrated under vacuum. The residue was stripped from acetic acid then lyophilized from t-butyl alcohol affording the trifluoroacetate (containing a 0.1 molar excess of trifluoroacetic acid) salt t-butyl alcohol (0.4 molar) solvate of the compound of Formula Ie as a white lyophil (589 mg; theory, 584 mg)

C. With stirring at −20° C. under argon isobutyl chloroformate (0.22 mL) was added to a solution of part (511 mg) of the product of part B of this example and N-methylmorpholine (0.18 mL) in dimethylformamide (8 mL). After 20 min hydroxylamine trimethylsilyl ether (0.40 mL) was added. Stirring was continued at −20° C. overnight and the reaction mixture was concentrated under vacuum. The residue was purified by column chromatography on silica gel by elution with ethyl acetate-pyridine-acetic acid-water (400:55:20:25, 500 mL; 300:55:20:25, 450 mL; 100:55:20:25, 500 mL). The residue from the fractions containing the product was stripped once from methanol and twice from ether, dried under high vacuum and lyophilized from t-butyl alcohol affording the t-butyl alcohol (0.4 molar) solvate of the compound of Formula If as a white lyophil (351 mg, 75–76% yield).

BIOLOGICAL PROPERTIES OF THE COMPOUNDS

As stated above the compounds of Formula I are matrix-metalloprotease inhibitors useful in treatment of disease in which matrix-metalloprotease promoted connective tissue remodelling is a causative factor, for example, rheumatoid arthritis and cancer. This utility is demonstrated by test of a compound in vitro against a collagenase matrix-metalloprotease, for example, human fibroblast collagenase, to determine whether the compound inhibits the action of the enzyme.

Human fibroblast collagenase was purified as described by Fields et al. (The Journal of Biological Chemistry, vol. 262, pp. 6221–6226, 1987), activated with trypsin and used at a concentration of 25 nM. H-Pro-Met-Ala-Leu-Trp-NHCH$_3$ (Netzel-Arnett et al., The Journal of Biological Chemistry, vol 266, pp. 6747–6755, 1991) was used as substrate at a concentration of 375 μM. Fluorescamine was used to detect the products of enzymolysis. The test compound was dissolved in an amount of dimethylsulfoxide such that the final concentration of dimethylsulfoxide after dilution in the test medium (aqueous 0.05 M tricine-0.2M calcium chloride, pH 7.5) did not exceed 5%. Product concentrations were measured at intervals throughout the test period (90 minutes). The half-maximal inhibitory concentration (IC50) of the test compound was calculated from the equation for a competitive inhibitor using percent inhibition values between 20% and 80%. The products of parts B and C of example 2 and parts B and C. of example 3 were tested and the following results were obtained.

| Inhibition of Human Fibroblast Collagenase | |
|---|---|
| Compound of Example | IC50 (μM) |
| 2B | 8.8 |
| 2C | 0.02 |
| 3B | 4.5 |
| 3C | 0.015 |

In the method of treating a mammal for a disease in which matrix-metalloprotease promoted connective tissue remodelling is a causative factor the effective amount of the compound of Formula I can be estimated from results of the above-described test. This aspect of the invention is contemplated to be carried out in any mammal in which matrix-metalloprotease promoted connective tissue remodelling is a causative factor, especially a human. It can be carried out using the compound of Formula I alone but is preferably carried out using a composition comprising the compound of Formula I and a pharmaceutically acceptable vehicle.

We claim:

1. A compound having the structural formula $$\underset{X}{\overset{O}{\|}}\diagdown\underset{}{\overset{CH_2R^1}{|}}\diagdown\underset{NH}{\overset{O}{\|}}\diagdown\underset{CH_2R^2}{\overset{}{|}}\underset{NH}{\overset{}{}}(CH_2)_m\diagdown SO_n\diagdown (CH_2)_p\diagdown NR^3R^4 \quad \text{Formula I}$$

wherein

X is HONH or HO;

$R^1$ is alkyl having from one to six carbon atoms;

$R^2$ taken together with $CH_2$ is the side chain of a natural amino acid or taken alone is alkyl having from one to six carbon atoms, phenyl or phenyl-lower-alkyl wherein phenyl is unsubstituted or substituted by hydroxy or lower-alkoxy, pyridyl, pyridyl-lower-alkyl, thienyl, thienyl-lower-alkyl, imidazolyl, imidazolyl-lower-alkyl, indolyl or indolyl-lower-alkyl;

$R^3$ taken alone is alkyl having from one to six carbon atoms;

$R^4$ taken alone is H or alkyl having from one to three carbon atoms; or, when $R^3$ and $R^4$ are both alkyl, the tertiary amine N-oxide; or $R^3$ and $R^4$ taken together with N are pyrrolidino, piperidino, azepino, morpholino or thiomorpholino or the N-oxide thereof or piperazino or N-methylpiperazino;

m is an integer from 2 to 6;

n is 0, 1 or 2;

p is an integer from 2 to 6; or a pharmaceutically acceptable acid addition salt or solvate or acid addition salt-solvate thereof.

2. A compound according to claim 1 wherein the carbon atom bearing $R^1CH_2$ has the R-configuration and the carbon atom bearing $R^2CH_2$ has the S-configuration.

3. A compound according to claim 2 wherein $R^1$ is isopropyl and $R^2$ is 3-indolyl.

4. A compound according to claim 3 wherein m is 2, n is 0 and p is 2.

5. A compound according to claim 4 wherein $R^3$ and $R^4$ taken alone are each methyl.

6. A compound according to claim 5 wherein X is HO.

7. A compound according to claim 5 wherein X is HONH.

8. A compound according to claim 4 wherein $R^3$ and $R^4$ taken together with N are morpholino.

9. A compound according to claim 8 wherein X is HO.

10. A compound according to claim 8 wherein X is HONH.

11. The method of treating a mammal for a disease in which matrix-metalloprotease promoted connective tissue remodelling is a causative factor which comprises administering the mammal a matrix-metalloprotease inhibiting amount of a compound according to claim 1.

* * * * *